(12) United States Patent
Devore et al.

(10) Patent No.: US 6,204,365 B1
(45) Date of Patent: *Mar. 20, 2001

(54) COLLAGEN MODULATORS FOR USE IN PHOTOABLATION EXIMER LASER KERATECTOMY

(75) Inventors: Dale P. Devore, Chelmsford, MA (US); Richard A. Eiferman, Louisville, KY (US)

(73) Assignee: Collagenesis, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,529

(22) Filed: Jan. 18, 1999

Related U.S. Application Data

(63) Continuation of application No. 08/602,922, filed on Feb. 16, 1996, now Pat. No. 5,861,486, which is a continuation of application No. 07/942,657, filed on Sep. 9, 1992, now Pat. No. 5,492,135.

(51) Int. Cl.$^7$ .............................. A61K 38/17; A61B 17/00
(52) U.S. Cl. .............................. 530/356; 514/801; 522/68; 128/858
(58) Field of Search .............................. 128/858; 522/68; 514/801; 530/356

Primary Examiner—Michael Borin
(74) Attorney, Agent, or Firm—Darby & Darby

(57) ABSTRACT

A method of smoothing irregular corneal surfaces and removing protuberances from corneal surfaces by photoablative eximer laser keratectomy is provided. Collagen compositions for use in making collagen modulators useful in photoablative procedures are described. These compositions are applied to irregular corneal surfaces in sufficient amounts to at least fill in depressions or other irregularities on a corneal surface and are converted into a modulator, as a gel or polymerized film, prior to photoablation. The collagen modulators facilitate the photoablative smoothing of irregular corneal surfaces and protect adjacent corneal tissue from undesired photoablation.

6 Claims, 11 Drawing Sheets

FIG. (1a) 
FIG. (1b) 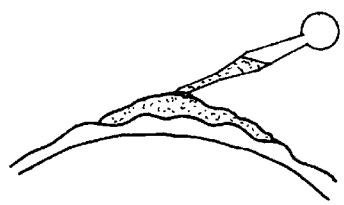
FIG. (1c) 
FIG. (1d) 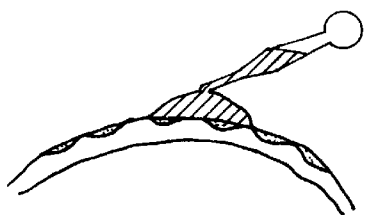
FIG. (1e) 
FIG. (1f) 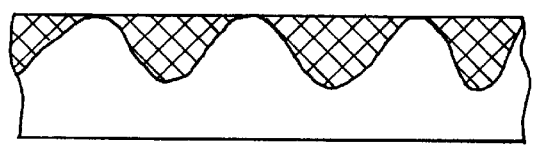
FIG. (1g) 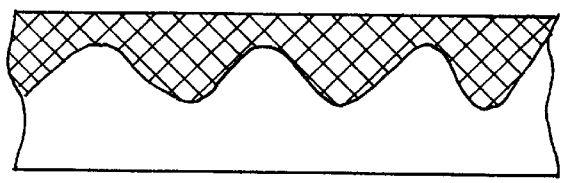

FIG. (2a) 
FIG. (2b) 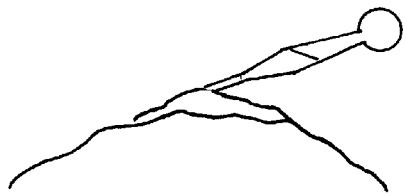
FIG. (2c) 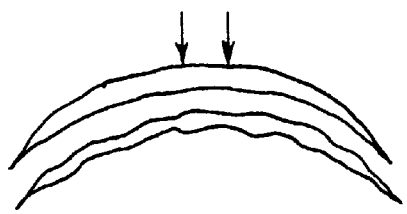
FIG. (2d) 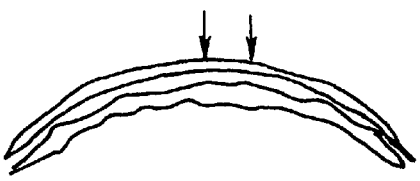
FIG. (2e) 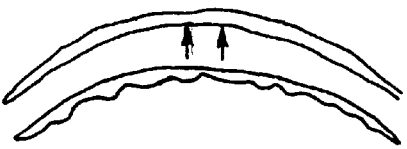
FIG. (2f) 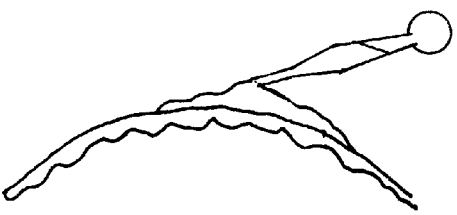
FIG. (2g) 

FIG. (3a)
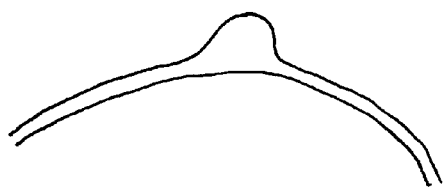
FIG. (3b)
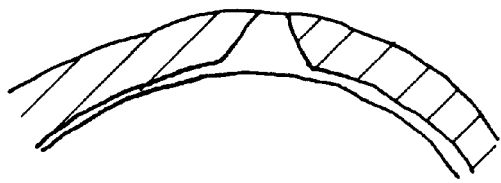
FIG. (3c)
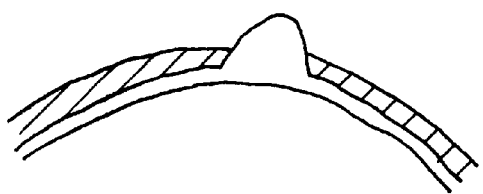
FIG. (3d)

FIG. (4a)
FIG. (4b)
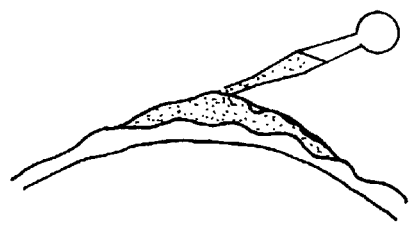
FIG. (4c)
FIG. (4d)
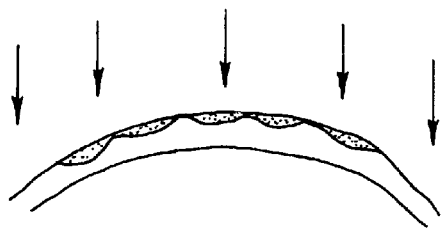

FIG. (5a)
FIG. (5b)
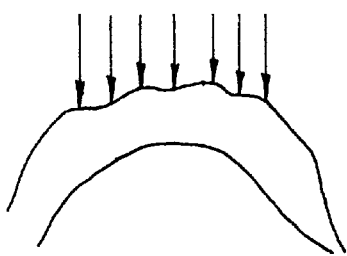
FIG. (5c)
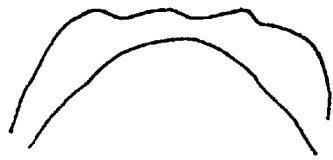
FIG. (5d)
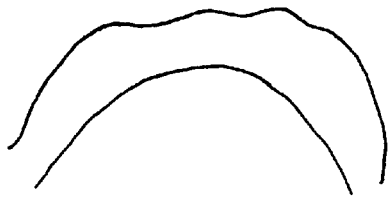
FIG. (5e)
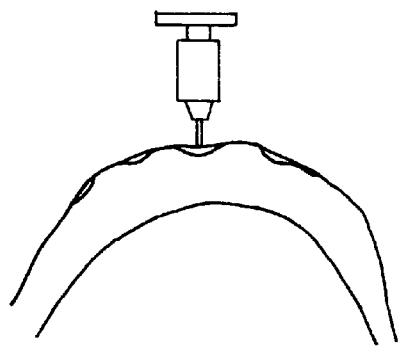
FIG. (5f)
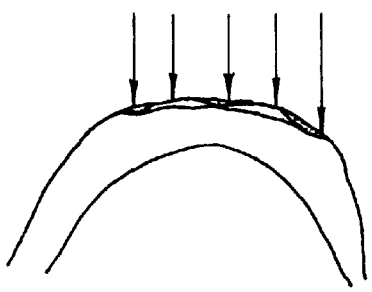
FIG. (5g)

COLLAGEN MODULATORS FOR USE IN PHOTOABLATION EXIMER LASER KERATECTOMY

This patent application is a continuation of application Ser. No. 08/602,922, filed Feb. 16, 1996, now U.S. Pat. No. 5,861,486 which is a continuation of Ser. No. 07/942,657, filed Sep. 9, 1992, now U.S. Pat. No. 5,492,135. Each of these prior applications is hereby incorporated herein by reference, in its entirety.

FIELD AND BACKGROUND OF THE INVENTION

Photoablation eximer laser keratectomy is a ophthalmologic technique which employs an 193 nm excimer laser as a surgical tool to ablate or remove a precise amount of tissue from the anterior corneal surface of the eye. In addition to its usual application in correcting refractive errors (e.g. myopia, hyperopia and astigmatism) by altering the curvature of the cornea, this technique has more recently been applied, with success, in removing opacities and irregularities from the anterior corneal surface.

The application of eximer lasers in photoablation procedures have been described in the medical literature. See, for example, Sher, N. A. (1991) *Arch. Ophthal.,* Vol. 109, pages 491–498; Zabel, R. W. et al. (1990) *Refrac. Corn. Surg.,* Vol. 6, pages 329–334; Steinert, R. F. et al, ibid, page 352; Gaster, R. N. et al. (1989) *Invest. Ophthal. Vis. Sci.,* Vol. 30, pages 90–98; and Tuft, S. J., ibid, page 1769–1777. Typically, a far ultraviolet argon fluoride laser, emitting at 193 nm, is used in clinical procedures because of its minimal tissue interaction, ablative efficiency and ease of control of ablation depth. Moreover, irradiation at 193 nm shows less mutagenic potential in comparison to longer ultraviolet wavelengths. The laser, fitted with a series of apertures of varying diameter and shapes, is preprogrammed to deliver a series of pulses of a given duration and energy fluence settings. In general, eye movements are minimized during the ablating process and the eye is held with the visual axis fixated under the center of the laser beam.

The extent and depth of the ablation depends on a number of variables which include aperture, shape and diameter, laser energy fluence ($mJ/cm^2$), duration of irradiation (nanoseconds), pulse rate (Hz) and number of pulses. Other factors would include intraoperative epithelium and corneal stromal drying during effluent removal. Eximer laser ablation of the anterior corneal lamellar tissue, in general, leaves behind a smooth surface that enables reepithelialization, a clearer cornea, and an appropriate refractive surface.

In certain situations, modulators are used during the procedure. As defined herein, the term "modulator" refers to a substance which, when applied to tissue, is capable of absorbing UV irradiation and modulating the degree of tissue ablation. Modulators are generally used as adjuncts to promote photoablative smoothing of irregular corneal surfaces and to protect adjacent corneal tissue where ablation is not desired. Examples which would benefit from the use of modulators include removal of corneal scars and opacities, often accompanied with an irregular or rough epithelial surface, due to post-infectious and post-traumatic causes, including herpes simplex virus, dystrophies (e.g. Salzmanns and Reis Buckler's syndrome), recurrent erosions and band keratopathy. Also, several types of corneal pathologies ablate more quickly than others, and this differential ablation may lead to increased irregularity of the corneal surface following ablation.

A number of photoablation modulators have been reported in the literature. See, for example, Sher, N. A. (1991), supra; Steinert (1990), supra; Kornmehl, E. W. et al. (1991) *Investigative Ophthalmology & Visual Science,* Vol. 31(4), Page 245, Abstract no. 1203; and Steinert, R. F. in "Eximer Laser Phototherapeutic Keratectomy: Strategies and Representative Cases," 17th Cornea Research Conference, Sep. 19–21, 1991, Eye Research Institute and Massachusetts Eye and Ear Infirmary. Examples of known modulators include viscous aqueous solutions of methylcellulose, dextran 70, sodium carboxymethylcellulose and hydroxypropylmethylcellulose 2910 as well as 0.9% saline.

In general, conventional modulators suffer from a number of deficiencies which preclude their broader use in photoablation procedures. For example, modulators (1) are difficult to apply smoothly on the corneal surgical bed; (2) are susceptible to drying and rippling from the air flow from the effluent remover; (3) do not adequately absorb at 193 nm; and/or (4) do not adequately promote a smoother ablated corneal surface relative to a control situation (no modulator) because the modulator ablates at a different rate than corneal tissue. Accordingly, there is a need in the art for photoablation modulators which avoid one or more of the aforementioned deficiencies.

SUMMARY OF THE INVENTION

Surprisingly, it has now been discovered that certain collagen formulations are useful for preparing collagen modulators useful in photoablation procedures. These compositions not only fill in various imperfections on the corneal surface, but also ablate at approximately the same rate as the corneal stroma. The collagen modulators promote a smoother ablated surface, relative to a control situation (no modulator). The disclosed collagen formulations has enormous utility in clinical eximer laser photoablation procedures.

The present invention provides biologically compatible collagen solutions for use in photoablation procedures and methods for its preparation as well as application in therapeutic and refractive eximer laser photoablation.

In one embodiment of the invention, a neutralized, acid solubilized collagen, which remains in solution at physiological temperatures, is used to prepare a modulator gel coating or film on a corneal surface. These solutions must be extensively dialyzed against EDTA solutions and/or deionized water to reduce available cations and to prevent premature collagen fibrillogenesis. As the cations are removed, the pH of the collagen solution is increased to between about 6.8 and about 7.5 by adjusting the pH of the EDTA solution using 1 N sodium hydroxide. The collagen preparation does not undergo typical fibrillogenesis in the absence of added unbound or free cations.

When applied to a surface of a human cornea prior to photoablation keratectomy, the collagen formulation uniformly coats and readily adheres to the surface, filling surface depressions and other irregularities and provides a smooth surface for subsequent photoablation. The collagen coating is then instantly converted to a firm gel upon contact with a metal cation-containing solution. Metal cations are supplied in buffer solutions such as phosphate buffered saline or sodium chloride solution. The collagen gel readily absorbs UV irradiation, e.g. 193 nm, which is used in eximer laser keratectomy and exhibits ablation properties which resemble the human cornea. Upon completion of the photoablation procedure, any remaining residual collagen gel are readily removed from the corneal surface by dislodging the residue with water or physiological buffer solution.

In another embodiment of the invention, chemically modified polymerizable soluble collagen solutions having redox initiators are used in preparing modulator films. When applied to a corneal surface as a coating, the chemically modified collagen adheres to the surface, filling surface depressions and other irregularities. The coating is then subjected to polymerization conditions such as short wave UV to form a thin modulator film prior to photoablation. The film strongly adheres to the corneal surface and is physically removed during the photoablative procedure.

In a further embodiment of the invention, a glutaric anhydride modified collagen, preparable by reacting soluble collagen with glutaric anhydride in an amount ranging between about 20 and about 30 wt. % based on total collagen, is provided and which undergoes temperature-dependent sol/gel transformation. The glutaric collagen, at a collagen concentration ranging between about 5 and about 100 mg/ml, melts or liquifies at physiological temperature, e.g. 37° C., to form a viscous solution. When applied to a corneal surface as a coating at 37° C., the glutaric collagen adheres to the surface, filling surface depressions and other irregularities. The coating rapidly forms a gel upon cooling to room temperature without any addition of metal cation solution or induced polymerization. The collagen gel readily absorbs UV irradiation, e.g. 193 nm, which is used in eximer laser keratectomy and exhibits ablation properties which resemble the human cornea. Upon completion of the photoablation procedure, any remaining residual collagen gel may be readily dislodged from the corneal surface with water or physiological buffer solution.

Accordingly, it is an object of the invention to provide a neutralized, acid solubilized collagen solution suitable for use in preparing a modulator for use in photoablation procedures and a method for its preparation. When such compositions are applied to the corneal surface as a coating, it does not undergo fibrillogenesis or gel formation unless contacted with cations.

It is another object of the invention to provide a chemically modified polymerizable collagen solution for use in preparing a collagen modulator and a method for its preparation. When applied to the corneal surface as a coating, the collagen solution is polymerized to form a film which is then removed by the photoablative procedure.

It is a further object of the invention to provide a method for smoothing an irregular corneal surface having collagen formulations as modulators by photoablation.

These and other objects of the invention will become apparent in view of the detailed description below.

BRIEF DESCRIPTION OF THE DRAWINGS

FIGS. 1 (a–e) illustrate the preparation of a neutralized soluble collagen modulator on a irregular corneal surface according to the method of the present invention. FIGS. (1f) and (1g) illustrate cross-sections of corneal surfaces having an adherent collagen modulator.

FIGS. 2 (a–g) illustrate the use of a contact lens to form a smooth collagen modulator coating on a corneal surface.

FIGS. 3 (a–d) illustrate the present method for removing a protuberance from a corneal surface using a collagen modulator.

FIGS. 4 (a–d) illustrate the preparation of a polymerized collagen modulator film, from a modified collagen solution, on a irregular corneal surface.

FIGS. 5 (a–g) illustrate the resulting corneal surfaces after photoablation without the use of a collagen modulator (FIGS. 5a–c) or with a collagen modulator (FIGS. 5d–g).

DETAILED DESCRIPTION OF THE INVENTION

Figure 6:
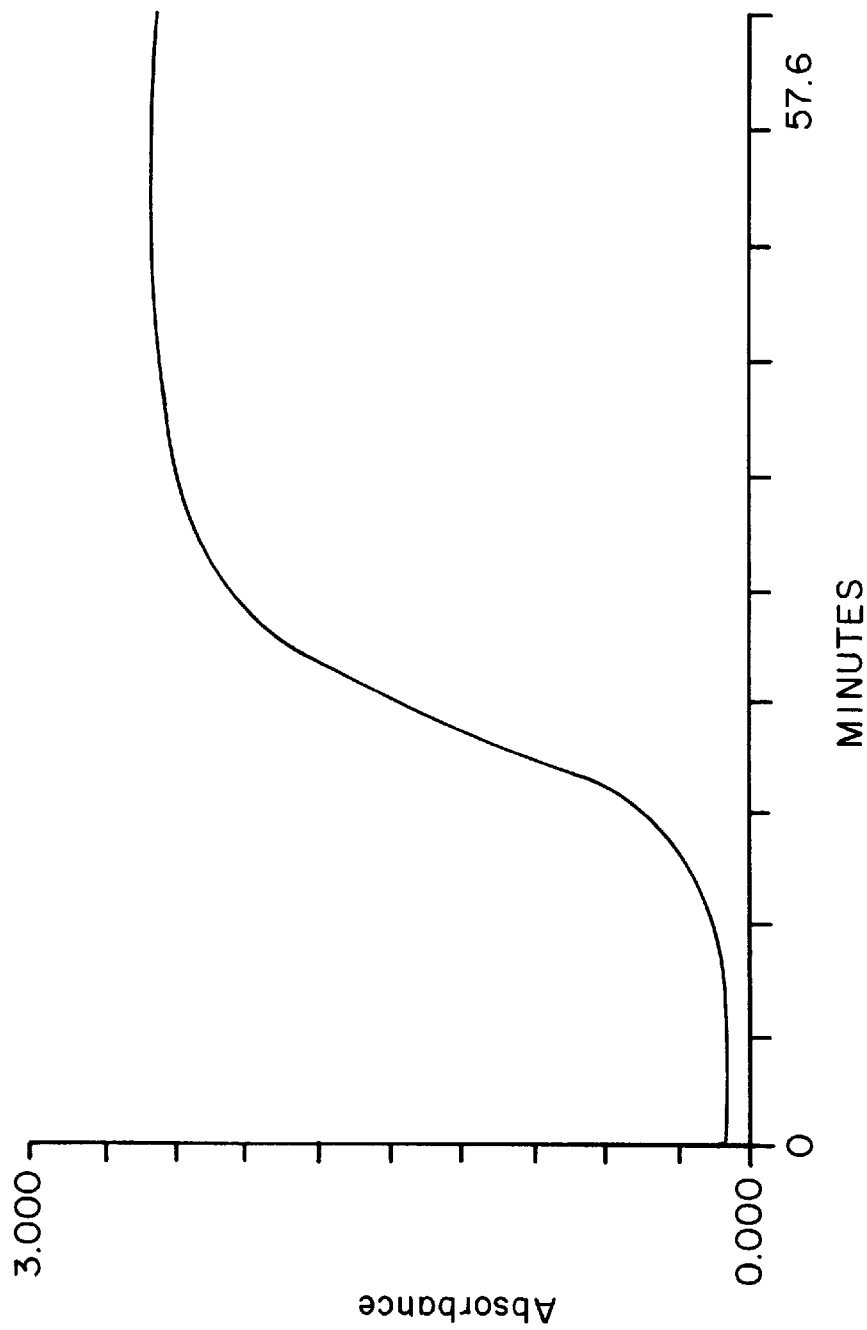
FIG. 6 illustrates that undialyzed, concentrated solubilized collagen solution (3.0 mg/ml), when adjusted to neutral pH (pH 7.2 using 2.5 N NaOH), undergoes fibrillogenesis at 25° C. The absorbance was monitored at 313 nm for a period of time up to 1 hour.

All patents, patent applications, and literature references are hereby incorporated by reference in their entirety.

The invention arose from the discovery that collagen compositions are useful in preparing modulators for use in photoablative procedures for smoothing irregular corneal surfaces and for protecting adjacent corneal areas surrounding corneal protuberances such as nodules or scars from undesired photoablation.

As defined herein, the term "biologically compatible" refers to collagen modified in accordance with the present invention which when incorporated or implanted into or placed adjacent to the biological tissue of a subject, does not induce an immune response or deleterious tissue reaction after such incorporation or implantation or placement; and the term "available cation" refers to metal ions which are releasably bound to collagen and which may be removed by dialysis.

The type of collagen useful in preparing the collagen modulators of this invention is selected from the following groups: purified Type I collagen, Type IV collagen and Type III collagen, solubilized collagen extracted from intact collagen-rich tissue or a combination of any of the foregoing. Preferred as a collagen starting material is purified Type I collagen derived from animal tissue or predominantly Type I collagenous product prepared from human tissue. Type I collagen is ubiquitous and readily extracted from animal tissues such as dermis and tendon. Type I collagen is the most abundant collagen in connective tissues, i.e., skin and tendon, and comprises up to 95% of the total collagen in skin and tendon. In contrast, type III collagen generally comprises up to 5% of total collagen in skin. Common sources are bovine tendon and hide and rat tail tendon. Extraction from human tissues is difficult. U.S. Pat. No. 4,969,912 and U.S. patent application Ser. No. 07/572,052, filed Aug. 23, 1990, describe unique methods to disperse and solubilize human tissue.

A variety of collagen solubilization procedures that are well known in the art may be used to prepare the modified collagen solutions useful for the instant invention. Native collagen is liberated from non-collagen connective tissue constituents, e.g. lipids, sugars, and aqueous soluble proteins, extracted from tissue by subjecting it to proteolytic enzymatic treatment by an enzyme other than collagenase. Suitable proteolytic enzymes include pronase and pepsin. The enzymatic treatment removes most of the immunogenic non-helical portions of native collagen (telopeptide) and provides a collagen material which is soluble in dilute acidic aqueous media. A solution containing the crude solubilized collagen is then subjected to a series of treatments to purify the soluble type I atelopeptide collagen by separating it from insoluble collagen, other types of collagen, and non-collagen products resulting from the proteolytic enzymatic procedure. Conventional methods for preparing pure, acid soluble, monomeric collagen solutions by dispersing and solubilizing native collagen are described, for example, in U.S. Pat. Nos. 3,934,852; 3,121,049; 3,131,130; 3,314,861; 3,530,037; 3,949,073; 4,233,360 and 4,488,911.

It will be understood that any suitable standard procedure may be employed to prepare a purified collagen solution from any suitable source so long as the material is undernatured, does not cause any deleterious effect on the delicate eye tissues, and is capable of undergoing gelation or fibrillogenesis under physiological conditions. A preferred method for preparing solubilized collagen solutions for use in practicing this invention is provided in Example 1 which describes preparation of a purified acid soluble Type I collagen solution from bovine hide, a readily available source of starting material.

The purified acid soluble collagen solution has a concentration, based on spectrophotometric determination of hydroxyproline content, broadly ranging between about 1 mg and about 20 mg of collagen, preferably between about 2 mg and about 5 mg, per ml of solution.

The presence of metal cations in acid solubilized collagen solutions, when adjusted to neutral pH at temperatures of 18° C. to 37° C., may initiate molecular interactions leading to premature collagen fibrillogenesis or gel formation, prior to application on a corneal surface. Hence, in practicing this invention, it is desirable that the acid solubilized collagen be treated to reduce the available cation concentration prior to and during neutralization. The resultant neutralized acid soluble collagen solution at room temperature or physiologial temperatures, i.e. 37° C., should be readily applied to the corneal surface as a liquid coating or film. This coating or film should remain in its liquid state and not undergo gelation unless contacted with an effective amount of a metal cation contained in a physiological acceptable solution.

Suitable, but not limiting, methods to reduce levels of available metal cations from solubilized collagen solutions include dialysis, diafiltration, column chromatography using desalting gels, and batch removal of organic salts using absorbent beads. The preferred method for reducing available metal cation levels present in a solubilized collagen solution is dialysis.

Dialysis is performed at least once against deionized water, with or without metal chelating agents, to reduce the available metal cation concentration to levels which effectively prevent occurrence of premature collagen fibrillogenesis or gelation under physiological conditions at 37° C. Dialysis reduces the amounts of calcium, magnesium, sodium, potassium and other available metal ions present in the purified collagen solution.

In practicing the invention, it is preferred that the solubilized collagen solution be initially dialyzed against an aqueous solution containing metal chelating agents. Suitable, but non-limiting, chelating agents include aminopolycarboxylic acids such as ethylenediamine tetraacetic acid, disodium salt dihydrate (EDTA). Preferred metal chelating dialysis solutions for use in the present invention are EDTA solutions having a concentration ranging between about 0.025 M and about 0.1 M, preferably about 0.03 M.

In the preferred embodiment of the invention, the collagen solution are dialyzed preferably three times against aqueous 0.05 M EDTA solution at a time period of about 24 hours per each dialysis step. The pH of the EDTA solution used in the first dialysis is preferably 4.5. In second and third dialysis steps, the pH of the EDTA solutions are increased to about 5.5 and about 7.0, respectively.

Thereafter, the collagen solution is dialyzed at least once against deionized water, for a period of about 24 hours, to effectively reduce the amount of metal chelator present in the collagen solution.

Extensive dialysis of EDTA dialyzed collagen solutions against deionized water, however, may result in premature gelation during dialysis. Thus, in practicing this invention it is desirable that some EDTA residue be retained in the collagen solution at levels which do not cause irritation to eye tissues. The amount of EDTA retained in the solution is generally between about 0.02 M and about 0.05 M, preferably between about 0.025 M and about 0.035M.

Upon completion of the dialysis, the dilute neutralized soluble collagen solution may be concentrated, if necessary, to a collagen concentration broadly ranging between about 1 and about 10 mg/ml, preferably between about 1 and about 5 mg/ml and most preferably about 3.0 mg/ml, based on spectrophotometric determination of hydroxyproline content. Suitable methods for concentrating a dilute collagen solution include lyophilization, ultrafiltration, and vacuum drying. A preferred method for concentrating the collagen solution is ultrafiltration.

Without being bound to any mechanism or theory of operation in this invention, it is believed that treatment of the acid solublized collagen solution with metal chelator-containing solutions (e.g. EDTA disodium solutions) and deionized water removes traces of free or unbound metal cations in the collagen solution and/or adjusts the ionic strength of the collagen solution which may initiate or promote premature self-assembly of collagen molecules into fibrils. The collagen self-assembly process is sensitive to a variety of parameters which include ionic strength, pH, temperature, and salt concentration of the solution. For a discussion, see, K. A. Piez and A. H. Reddi, ed. in "Extracellular Matrix Biochemistry," Elsevier Publishers; New York, USA, pages 14–28, and Nimni, M. E., ed. in "Collagen: Vol. I Biochemistry," CRC Press, Inc.; Boca Raton, Fla., USA (1988), pages 1–33 and 113–137.

In one embodiment of the invention, the neutralized soluble collagen solution is used to prepare a modulator, in the form of a gel, on a corneal surface prior to photoablation. The collagen-solution is applied to the corneal surface in an amount effective to-at least fill in surface depressions and other irregularities. The solution readily adheres to the surface, filling surface depressions and other irregularities and provides a smooth surface for subsequent photoablation. It is preferred that the epithelium on the corneal surface be removed, e.g. by abrasive scraping or other appropriate techniques, prior to applying the collagen solution.

The collagen solution may be applied in any suitable manner to at least fill in surface depressions or irregularities. If desired, the collagen solution may be applied to the corneal surface in amounts to at least provide a uniform coating on the corneal surface. Suitable, but non-limiting, application methods include dropwise addition using a sterile pipet or a syringe needle (gauge 16 to gauge 30), brushing and spraying. FIGS. 1 (a–e) illustrate an example of applying a neutralized, soluble collagen solution onto an irregular corneal surface. A flowable neutralized soluble collagen solution is applied (FIG. (1b)) to an uneven corneal surface (FIG. (1a)) in an amount to at least fill in depressions or other irregularities (FIG. (1c)). Thereafter, a metal cation in a physiological medium is applied to the collagen coating (FIG. (1d)) to convert it to a collagen modulator in a form of a gel (FIG. (1e)).

Collagen solutions having a concentration greater than 5 mg/ml do not flow easily to form a uniform coating on a surface. In such cases, a contact lens is applied over the solution to assist in forming a uniform layer of collagen. The application of a contact lens or other such device of known diameter and base curvature that conforms to the shape of the corneal surface is expected to cause the modulator solution to form a smooth and uniform surface for subsequent ablation. FIGS. 2 (a–g) illustrate the application of a contact lens to form a smooth modulator-coated surface on the cornea. FIG. (2a) shows an uneven, irregular corneal surface to which a neutralized solubilized collagen solution is applied (FIG. (2b)). Thereafter, a contact lens or molding device is placed over the collagen solution (FIG. (2c)) to uniformly spread the solution over the corneal surface (FIG. (2d)). The device is then removed (FIG. (2e)) and a metal cation solution is applied (FIG. (2f)) to the collagen coating which converts it into a modulator gel (FIG. (2g)).

In practicing the invention, any amount of collagen solution may be applied to the corneal surface which is effective to at least fill in surface depressions and other irregularities. It will be understood by the skilled practitioner that the effective amount of collagen solution employed is dependent, for instance, on the condition of the corneal surface, the extent of photoablation required to smooth the surface, and the concentration of the collagen solution. FIG. (1f) illustrates a cross-section of a smooth corneal surface ready for photoablation; the corneal surface has an adherent collagen modulator coating which at least fills in depressions and other irregularities on a corneal surface. FIG. (1g) illustrates a cross-section of smooth corneal surface ready for photoablation; the corneal surface has an adherent collagen modulator as a smooth uniform coating or film on the corneal surface.

For smoothing of irregular corneal surfaces, the effective amount of collagen solution applied is one that at least fills in surface depressions and other irregularities. In practicing the invention, a modulator coating having a thickness ranging between about 10 microns and about 100 microns from the corneal surface, preferably about 50 microns, is preferred.

In the case of corneal surfaces having protuberances, e.g. raised corneal scars or nodules, the thickness of the modulator coating is preferably equal to the height of the protrusion. If desired, the coating may be applied exclusively to areas surrounding the protuberance to protect these areas from undesired photoablation. FIGS. 3 (a–d) illustrate examples of applying collagen solutions on corneal surfaces having a protuberance. FIG. (3a) illustrates a corneal surface having a protuberance; FIG. (3b) show the corneal surface of FIG. (3a) having an adherent collagen modulator of approximately the same height as the protuberance while FIG. (3c) shows the collagen modulator surrounding the protuberance and protecting the adjacent areas from undesired photoablation. FIG. (3d) shows a smooth corneal surface following photoablation.

Thereafter, the collagen coating is contacted with an amount of a metal cation in a physiologically acceptable solution effective to convert the collagen coating into a modulator in the form of a gel.

Suitable, but non-limiting, metal cations include sodium, potassium, magnesium and calcium in the form of salts. Suitable but non-limiting, examples of salts include the metal chlorides, bromides, iodides, phosphates, sulfates, acetates. These metal ions are preferably delivered in a carrier such as a physiologically acceptable solution. e.g water or aqueous buffer solutions. The metal cation solution may contain one or more types of metal ions. In practicing the invention, the preferred metal cation solutions are phosphate buffered saline or water solution having a 2.5 M sodium chloride concentration.

The metal cation solutions are applied to the collagen coating in any suitable manner which does not substantially displace the collagen from surface depressions or adversely affect the uniformity of the collagen coating. Application methods include spraying, dropwise addition, and the like. A preferred method is slowly adding saline solution in a dropwise or dribbling fashion to the collagen coating. FIG. (1d) illustrates an method of applying a cation-containing solution to a collagen-coated corneal surface. Upon formation of collagen gel, excess metal cation solution may be removed using an appropriate absorbent material, e.g. tissue paper or sponge, prior to photoablation.

Without being bound to any mechanism or theory of operation in this invention, it is believed that the cation-exposed solubilized collagen molecules undergo some degree of self-assembly to form microfibrils which may be observed microscopically; a visible "gelation" or gel formation of the collagen molecules occurs. As collagen molecules continue to interact, the "gel" becomes more opaque as microfibrils and reconstituted fibrils form. The gelation is believed to be an early event in fibrillogenesis and a phenomenon observed using dilute collagen concentrations. For a discussion of the fibrillogenesis process, see Nimni, M. E. "Collagen: Vol. I Biochemistry," CRC Press, Inc.; Boca Raton, Fla., USA (1988), pages 7–16 and Silver, F. H. in "Biological Materials: Structure, Mechanical Properties, and Modeling of Soft Tissues", New York University Press, New York; N.Y. (1987), pages 137–163.

In another embodiment of the invention, chemically modified polymerizable soluble collagen solutions are used to prepare collagen modulatorson a corneal surface. When applied to a corneal surface, the chemically modified collagen adheres to the surface and fills in depressions and other irregularities on the corneal surface. The amounts and methods for applying the modified collagen to a corneal surface are described above. In practicing the invention, it is preferred that the epithelium be removed, by suitable methods, prior to collagen application.

Thereafter, the applied modified collagen is subjected to polymerization conditions, e.g. using short wave UV, to form a thin polymerized film on the corneal surface. Short wavelength UV (254 nm) induces free radical polymerization of aromatic amino acids present in collagen. Chemical initiators of free radical formation, such as sodium persulfate, may be optionally added to the collagen coating to accelerate UV polymerization. The polymerized film firmly adheres to the corneal surface and is physically removed during the photoablative procedure. FIGS. 4 (a–d) illustrate formation of a polymerized modified collagen modulator film on a irregular corneal surface. A flowable modified collagen solution containing a redox initiator is applied (FIG. (4b)) to an uneven corneal surface (FIG. (4a)) in an amount to at least fill in depressions or other irregularities to form a smooth surface (FIG. (4c)). Thereafter, the surface (FIG. (4d)) is irradiated with short wave UV which polymerizes the collagen coating into a modulator film.

A number of modified polymerizable collagen solutions which are useful in practicing the invention may be used. See, for example, U.S. Pat. No. 4,969,912 and co-pending U.S. patent applications Ser. No. 486, 558, filed Feb. 28, 1990; Ser. No. 547, 458, filed Jul. 3, 1990, and Ser. No. 646, 944, filed Jan. 29, 1991, which describes modified cross-linkable collagen solutions and methods for their preparation.

Useful modified collagen compositions which are suitable for use in making polymerized modulator films or coatings are based on purified solubilized collagen which are chemically modified with acylating agents, sulfonating agents, or combinations thereof. Such agents, in non-toxic effective amounts, may be safely employed in preparing a modified collagen modulator.

In practicing this invention, chemically modified collagen is prepared by reacting soluble collagen with at least one acylating agent which includes aliphatic, alicyclic and aromatic anhydrides and acid halides. Non-limiting examples of acylating agents include glutaric anhydride, succinic anhydride, lauric anhydride, diglycolic anhydride, methylsuccinic anhydride, methyl glutaric anhydride, dimethyl glutaric anhydride, succinyl chloride, glutaryl chloride, lauryl chloride, phthalic anhydride, methacrylic anhydride, trifluoroacetic anhydride, styrene/maleic anhydride co-polymer, and ethylene/maleic anhydride copolymer. These chemicals are available from Aldrich Chemical Company (Milwaukee, Wis.). A particularly preferred acylating agent for use in preparing a modified collagen composition which is suitable for use in the present invention is glutaric anhydride. An effective amount of an acylating agent is broadly between about 0.5 and about 30 wt. % total collagen, preferably between about 2 and about 20 wt. % total collagen in solution.

Useful sulfonating agents for the preparation of modified collagen compositions for use in the present invention include aliphatic, alicyclic and aromatic sulfonic acids or sulfonyl halides. Non-limiting examples of sulfonating agents for use in preparing collagen modulators include anthraquinone-1,5-disulfonic acid, 2-(chlorosulfonyl)-anthraquinone, 8-hydroxyquinoline sulfonic acid, 2-naphthalene- sulfonyl chloride, beta-styrene sulfonyl chloride, 2-acrylamido-2-methyl-1-propane sulfonic acid, aniline-2-sulfonic acid, fluorosulfonylbenzene sulfonyl chloride, quinoline sulfonyl chloride and poly (vinyl) sulfonic acid. These chemicals are also available from Aldrich Chemical Company (Milwaukee, Wis.). Preferred sulfonating agents are beta-styrene sulfonyl chloride, and quinoline sulfonyl chloride. An effective amount of sulfonating agent is broadly between about 0.5 and about 30 wt. % of the total collagen, preferably between about 2 and about 20 wt. % of the total collagen in solution.

Non-limiting combinations of acylating agents and/or sulfonating agents include glutaric anhydride/beta-styrene sulfonyl chloride/methacrylic anhydride; glutaric anhydride/ethylene/maleic anhydride copolymer/methacrylic anhydride; glutaric anhydride/polyvinyl sulfonic acid/methacrylic anhydride; and glutaric anhydride/ethylene/maleic anhydride copolymer/styrene/maleic anhydride copolymer. Preferred combinations for use in preparing modified collagen modulators include glutaric anhydride/beta-styrene sulfonyl chloride; glutaric anhydride/phthalic anhydride; and glutaric anhydride/aniline-2-sulfonic acid.

When combinations of two or more acylating agents, sulfonating agents, or mixtures of both agents are used for preparation of modified collagen composition, the total amount of chemical modifiers is preferably between about 2 and about 20 wt. % of collagen in solution.

Modification of collagen is carried out at alkaline pH, in a range between about 7.5 and about 10.0, preferably between about 8.5 and about 9.5, and most preferably at about pH 9.0. The acylation reaction may be monitored more accurately by grossly observing a decrease in pH. The reaction is terminated when the pH value remains stable at between about 5 and about 8, preferably between about 6.5 and about 7.5. The reaction may also be monitored by removing aliquots and measuring the free amine concentration of the modified collagen solution as compared to the starting solution of collagen.

The modification reaction should be complete in between about 5 and about 90 minutes, preferably between about 20 and about 40 minutes. The reactions should be carried out at temperatures between about 0° C. and about 37° C., preferably between about 4° C. and about 25° C.

The reaction may be stopped by adjusting the pH to about 12.0 for about 2 minutes. This destroys the residual, unreacted chemical modifier. The modified collagen is then precipitated by reducing the pH using hydrochloric acid, acetic acid, nitric acid, sulfuric acid, or other acid.

The amount of acid must be sufficient to precipitate out the chemically modified collagen. Generally precipitation occurs at a pH between about 3.5 and about 6.0, preferably between about 4.0 and about 5.0.

The precipitate of reacted collagen which now contains substituent groups reacted with amine groups (primarily epsilon-amino groups), is recovered from the mixture using conventional techniques such as centrifugation or filtration. Centrifugation at between about 3,000 and about 15,000 rpm for between about 20 and about 60 minutes, preferably between about 4,000 and about 12,000, for between about 20 and about 30 minutes provides efficient recovery of the precipitate.

After recovery, the precipitate is washed with deionized water and subsequently dissolved in a physiological solution, e.g., phosphate buffer (0.1 M) at about pH 7.2. It may be necessary to adjust the pH between about 7.0 and about 7.5. This may be done, for example, by the addition of sodium hydroxide solution.

Following dissolution of the precipitate, the solution is generally filtered by conventional filtering means, i.e. a 5 micron filter, and then centrifuged to remove air bubbles. At this point, the resulting solution containing chemically modified collagen molecules and aggregates exhibits a viscous consistency, varying degrees of transparency and clarity, and a characteristic refractive index depending on the choice of chemical modifiers, the extent of acylation and on the state of solubility of the starting collagen material.

The chemically modified soluble collagen composition has a collagen protein concentration broadly ranging between about 5 and about 100 mg per ml of solution, preferably between about 5 and about 50 mg per ml and most preferably between about 5 and about 10 mg per ml.

The viscosity of the modified collagen solution, as determined at a temperature of about 25° C., broadly ranges between about 3,000 centipoise and about 30,000 centipoise, preferably between about 3,000 and about 75,000 centipoise and most preferably about 5,000 centipoise. Viscosity of the solution may be adjusted by the addition of buffer or collagen precipitate.

The polymerization or crosslinking of the modified collagen compositions may be carried out by simply exposing the material to short wave UV (e.g. 254 nm) and atmospheric oxygen. However, the rate of polymerization is not practical for use during the excimer laser procedures. The rate of polymerization may be dramatically increased by adding appropriate redox initiators to the collagen composition followed by exposure to short wavelength UV irradiation. Without such an initiator, UV polymerization, even in the absence of oxygen, requires at least 10 minutes.

Prior to polymerization of the modified collagen solution, a suitable initiator is added to the solution either prior to or after application of the modified collagen composition onto the corneal surface. In practicing this invention, it is preferred that the initiator be added to the collagen composition prior to its-application onto the corneal surface.

Suitable, but non-limiting, examples of initiators include sodium persulfate, sodium thiosulfate, ferrous chloride tetrahydrase, sodium bisulfite and oxidative enzymes such as peroxidase or catechol oxidase. A suitable dosage of the chemical initiator is one that sufficiently promotes polymerization of the modified collagen within between about 30 seconds and about 2 minutes, preferably between about 30 seconds and about 1 minute, but insufficient to cause oxidative damage to corneal tissue. In practicing this invention, it is preferred that the amount of initiator is generally between about 0.5 and about 5 wt. % preferably less than about 1 wt. % based on total collagen concentration to reduce tissue oxidation.

Polymerization by UV irradiation may be accomplished in the short wave length range by using a standard 254 nm source or UV laser sources. With a standard 254 nm source of between about 4 and about 12 watts, polymerization generally occurs in between about 30 seconds and about two minutes, preferably no longer than 1 minute, at an exposure distance of between about 2.5 and about 10 cm, preferably between about 2.5 and about 5 cm distance. Because excess UV exposure will begin to depolymerize the collagen polymers and cause eye damage, it is important to limit UV irradiation for short periods. At 254 nm, the penetration depth is very limited.

In yet another embodiment of the invention, a glutaric anhydride-modified collagen modulator is provided which undergoes extensively temperature-dependent sol/gel transformations. This extensively modified collagen is preparable by reacting acid soluble collagen having a collagen protein concentration ranging between about 1 and about 10 mg per ml solution with glutaric anhydride in an amount ranging between about 20 and about 30 wt. % total collagen. The chemical modification reaction conditions and reconstitution of the modified collagen are the same as described above. The reconstituted glutaric collagen solution for use in making the collagen modulator has a collagen concentration broadly ranging between about 5 and about 100 mg per ml solution, preferably between about 5 and about 50 mg per ml solution and most preferably about 10 mg per ml.

The glutaric collagen melts or liquifies at physiological temperature, e.g 37° C., yet rapidly forms a gel at room temperature without addition of cation solution or induced polymerization. In practicing the invention, the glutaric collagen is first preheated to about physiological temperature prior to application to the corneal surface. Thereafter, the glutaric collagen coating cools to room temperature and undergoes gelation co form a smooth modulator gel surface ready for photoablation.

Corneal surfaces having an adherent collagen modulator, as a gel or polymerized film, are then subjected to the standard procedures used in photoalblation. The laser sources employed in the photoablation procedure are preferably non-thermal lasers such as an ultraviolet-or excimer laser. However, thermal or infra-red lasers may also be used. The ultraviolet lasers are currently preferred as they provide precise beams of energy which break apart protein bonds, ablating or vaporizing the cornea as opposed to burning the cornea as caused by thermal lasers. Of course, a wide variety of lasers or other radiation sources may be provided within the spirit and scope of the invention.

Particularly preferred are ultraviolet lasers such as the excimer type of far-ultraviolet laser. Such lasers, charged with argon-fluoride gas, have been shown to precisely ablate corneal tissue at wavelengths of 193 nm. The laser output of such a laser may be pulsed with typical pulse energies of more than 300 m$^3$ at a repetition rate of as much as 400 pulses per second. Alternatively, radiation from a frequency doubled or quadrupled Nd:YAG laser may be employed giving frequencies in the ultraviolet range.

FIGS. 5 ($a$–$g$) illustrates post-ablated surfaces, with or without the presence of a collagen gel modulator. When a collagen modulator is employed in smoothing operations, a smooth ablated corneal surface (FIGS. 5$d$–$g$) is obtained relative to a control surface (FIGS. 5$a$–$c$) having no modulator thereon. Application of an eximer laser (FIG. (5$b$) to an irregular corneal surface (no modulator present) produced a flattened cornea having irregularities. In contrast, application of an eximer laser (FIG. 5($f$)) to an irregular corneal surface (FIG. 5$d$) having a collagen modulator (FIG. (5$e$) resulted in a smooth corneal surface (FIG. (5$g$)).

Upon completion of the photoablation procedure, any remaining residual neutralized soluble or modified collagen modulator gel may be readily removed from the corneal surface. Suitable methods for removing the gel include spraying with water or a physiological acceptable buffer such as saline solutions. Collagen modulators in the form of a polymerized film, however, are physically removed by the photoablation process.

Methods for performing therapeutic excimer laser keratectomy have been described extensively in the medical literature. It is anticipated that numerous improvements or refinements in therapeutic laser photoablation will be made in the future. The application of the collagen modulators of invention in the improved techniques is within the spirit and scope of the invention.

In addition to its application as an adjunct in therapeutic photoablation, it is anticipated that collagen modulators would be broadly useful as removable surface mask to protect surfaces from undesired exposure to laser sources and to modulate the ablative effect of the laser. For example, the. collagen modulators may be used as an adjunct in photographic and lithographic processes and in circuit board manufacture.

The examples set forth below are intended to illustrate the invention without limiting its scope.

EXAMPLE 1

Preparation of Neutralized Acid Soluble Type I Collagen Solution

Fibrous Type I collagen was extracted from bovine material (calf hide) using the following procedure:

Clean, dehaired split hides were purchased from the Andre Manufacturing Co. (Newark, N.J.) and frozen until ready for use. Approximately 200 g of calf hide were thawed at room temperature and cut into approximately 1 cm$^3$ pieces using a scalpel and tweezers. The weight of the wet tissue was recorded. The calf hide was then placed into 15 liters of 0.5 M acetic acid and stirred with a lightening mixer at room temperature for at least one hour. A 10 ml solution of 0.5 M acetic acid containing 2% w/w (or 3.9 g) pepsin from porcine mucosa (Sigma Chemicals, St. Louis, Miss.) was added to the calf hide solution. This solution was stirred overnight with a lightening mixer at room temperature. An additional 10 ml 0.5 M acetic acid solution containing 1% w/w (or 1.96 g) pepsin was added to the calf hide mixture. The solution was again stirred overnight with a lightening mixer at room temperature. The dissolved calf hide solution was refrigerated overnight until a uniform temperature of 4° C. was reached. The pH of the solution was adjusted to 9.0 with 10 N NaOH to denature pepsin. Stirring was maintained throughout the pH adjustment process with a lightening mixer. As collagen will precipitate out at pH 9.0 when the temperature is above 6° C., ice cubes were added directly to maintain the 4° C. temperature. The solution is then refrigerated for at least four hours and then centrifuged at 4° C. for 30 minutes at 9000 rpm. The resulting pellet, containing pepsin, was discarded. The supernatant, containing collagen, was subjected to a series of purification steps.

The collagen solution was subjected to a diafiltration process to remove residual pepsin and low molecular weight components. An Amicon Model DC10L/DC10LA ultrafiltration system with a spiral membrane cartridge (SY0100) with a 100,000 kD molecular weight cut off was used.

Thereafter, collagen was precipitated out by adding solid NaCl to the supernatant to give a final NaCl concentration of 2.5 M. The solution was stirred at room temperature for at least two hours. The collagen precipitate was collected by centrifugation of the solution for 30 minutes at 9000 rpm and redissolved in 15 liters of 0.5 M acetic acid, a process requiring at least 2 hours. Collagen was reprecipitated out again by addition of solid NaCl to the solution to a final concentration of 0.8 M. The solution was stirred for at least two hours and the collagen collected by centrifugation of the solution for 30 minutes at 9000 rpm. This redissolving/precipitation procedure was repeated once more. The final pellet, containing purified collagen, was dissolved in 0.1 M acetic acid of sufficient volume to provide approximately 0.3 % w/w collagen Type I solution of pH 3.0. The collagen solution was then filtered through a 0.45 micron filter to remove particulate matter and sterilized through a 0.22 micron filter. The acid solubilized collagen solution contains a collagen concentration of about 3.0 mg/ml and a cation concentration as follows: calcium (0 mg/L), magnesium (0 mg/L), potassium (6.86 mg/L), and sodium (376 mg/L).

FIG. 6 shows that when undialyzed, concentrated solubilized collagen solution (3.0 mg/ml) is adjusted to neutral pH (pH 7.2 using 2.5 N NaOH), fibrillogenesis occurred at 25° C. The absorbance was monitored at 313 nm for a period of time up to 1 hour.

The acid solubilized collagen solution was then dialyzed against 0.05 M EDTA (99+% A.C.S., disodium salt dihydrate, Aldrich Chemical Co., Milwaukee, Wis., USA) at a ratio of 1 volume of collagen per 40 volumes of dialyzing solution. Dialysis was conducted using Spectra/Por 1 dialysis membrane tubing with a molecular weight cutoff of 6,000–8,000 (Spectrum Medical Industries, Inc., Los Angeles, Calif., USA). Three dialysis steps were conducted each for 24 hours and at a temperature of 25° C. The collagen solution was then dialyzed two more times, against fresh EDTA solution with pH adjustments to 5.5 and then to 7.0. Thereafter, the collagen solution was dialyzed against deionized water for 24 hours. The resulting neutralized acid soluble solution (50 ml) had a pH of 6.8, a collagen protein concentration of about 3.0 mg/ml, and a cation concentration as follows: calcium (0 mg/L), magnesium (0 mg/L), potassium (2.35 mg/L), and sodium (6900 mg/L). The solution was filtered through a sterile 0.2 micron filter (Millipore, Bedford, Mass., U.S.A.).

Aliquots of the dialyzed neutralized collagen solution were concentrated using two methods: (1) placing 10 ml in a sterile petri dish in the Sterile-guard laminar flow hood at 24° C. for 18 hours and (2) placing 10 ml of the dialyzed collagen solution in an Amicon stirred cell system containing a 100,000 MW cutoff filter (Amicon, Beverly, Mass., USA). About 40 pounds of pressure were applied using a nitrogen source until the collagen concentration was increased to about 5.5 mg/ml. The material, taken from both concentration methods, did not undergo gelatin or fibrillogenesis when incubated at 37° C. for 1 hour.

To evaluate gelation, a 0.1 ml volume of each of the above preparations were placed on a teflon surface and irrigated with about 0.3 ml of 3 M sodium chloride solution. The collagen immediately formed a firm gel which could be removed from the teflon surface using a spatula. The gel was clear and transparent. After incubation at 37° C. for 10 minutes, the gel became slightly opaque due to fibrillogenesis.

Figure 7:
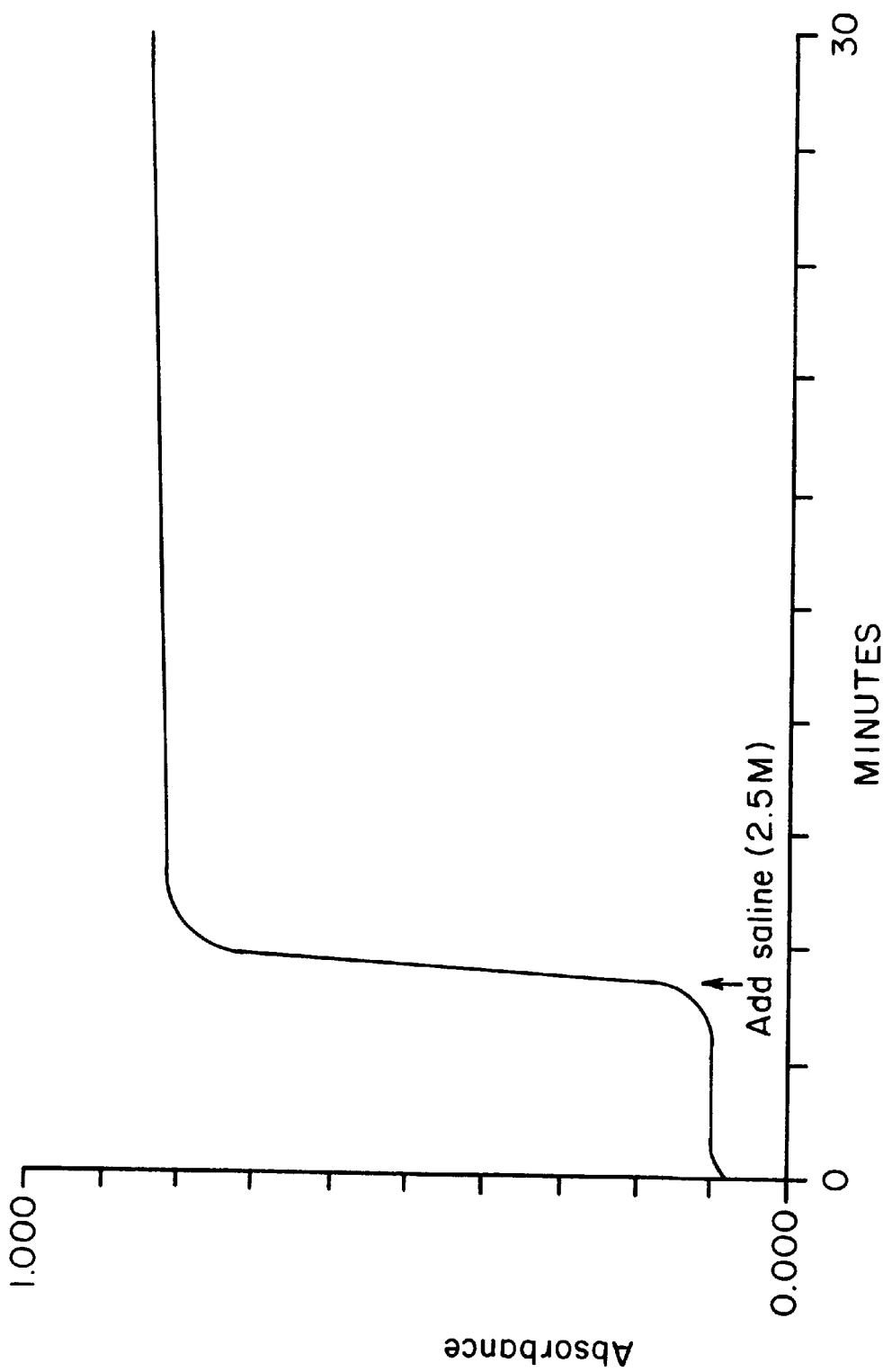
FIG. 7 illustrates the effect of addition of 0.5 ml of 2.5 M saline solution to 0.5 ml of neutralized acid soluble collagen solution (3.0 mg/ml) at 25° C. The sharp increase in absorbance (at 313 nm) indicates that the collagen solution immediately converts into a dense gel upon addition of saline solution.

FIG. 7 shows the effect of adding 0.5 ml of 2.5 M saline solution (pH 7.0) to 0.5 ml of the neutralized acid soluble collagen solution. Upon addition of saline, the collagen solution rapidly converted into a gel as evidenced by the sharp increase in absorbance (313 nm).

EXAMPLE 2

Preparation of Glutaric Anhydride Collacen Solution

In this Example, a pure, acid solubilized collagen was prepared as described in Example 1 without the subsequent dialysis steps. The collagen solution (3.0 mg/ml) was diluted to 2.8 mg/ml with 0.1 M acetic acid and filtered through a sterile 0.2 micron filter. The solution (100 ml) was adjusted to pH 9 and 7 mg (2.5 wt. %) of glutaric anhydride was added. The modification reaction proceeded for 20 minutes at 25° C. Thereafter, the pH was decreased to pH 4.3 to precipitate out the modified collagen. The precipitate was recovered by centrifugation and was washed three times with deionized water. The washed precipitate was very fine and granular. This material was dissolved in 10 ml of phosphate buffer (4 mM, pH 7.8) and the resultant solution was adjusted to pH 7.4 with 1 N NaOH. Thereafter, the solution was filtered through a sterile 5 micron filter unit. The modified collagen solution was viscous, clear, and transparent. The collagen concentration was about 25 mg/ml.

EXAMPLE 3

Preparation of an Extensively Modified Glutaric Anhydride Collagen Solution

In this Example, a pure, acid solubilized collagen was prepared as described in Example 1 without the subsequent dialysis steps; The collagen solution (3.0 mg/ml) was diluted to 2.8 mg/ml-with 0.1 M acetic acid and filtered through a sterile 0.2 micron filter. The solution (100 ml) was adjusted to pH 9 and 56 mg, (20 wt. %) of glutaric anhydride was added. The modification reaction proceeded for 20 minutes at 25° C. Thereafter, the pH was decreased to pH 4.3 to precipitate out the modified collagen. The precipitate was recovered by centrifugation and was washed three times with deionized water. The washed precipitate was very fine and granular. This material was dissolved in 10 ml of phosphate buffer (4 nM, pH 7.8) and the resultant solution was adjusted to pH 7.4 with 1 N NaOH. Thereafter, the solution was filtered through a sterile 5 micron filter unit. The modified collagen solution was viscous, clear, and transparent. The collagen concentration was about 30 mg/ml.

EXAMPLE 4

Preparation of Quinolone Collagen Solution

In this Example, a pure, acid solubilized collagen was prepared as described in Example 1 without the subsequent dialysis steps. The collagen solution, at a concentration of 2.2 mg/ml in 0.1 M acetic acid, was filtered through a sterile 0.22 micron filter. The solution (about 200 ml) was adjusted to pH 9 with 10 M NaOH and 1 M NaOH and 40 mg (9 wt. % based on total collagen) of quinoline sulfonyl chloride was added as a solid. The modification reaction proceeded for 60 minutes at 25° C. while maintaining the pH at about 9.0. Thereafter, the pH of the solution was reduced to pH 7 and the solution was filtered sequentially through a 0.45 micron filter and 2.2 micron filter. The filtered modified collagen solution was precipitated by reducing the pH to 4.6 using 6 N HCl and 1 N HC1. The precipitate was recovered by centrifugation and washed three times with sterile deionized water. The final precipitate was dissolved in phosphate buffered glycerol (4 mM phosphate buffer, 2.2% glycerol, pH 7.8) and adusted to pH 7.2 using 1 N NaOH. The modified collagen solution was filtered through a 5 micron filter and deaerated by centrifugation at 3500 rpm (IEC Model HN-F2 (DAMON/IEC Division, Needham, Mass., USA). The collagen material, at a concentration of about 5 mg/ml, was clear, viscous, and transparent.

EXAMPLE 5

Preliminary Evaluation of Neutralized Acid Soluble Collagen as Modulators

Samples of neutralized acid soluble collagen solution (5.5 mg/ml), prepared in accordance with Example 1, and saline solution at about 3.25 M were evaluated using a Tauntan LV 2000 eximer laser (VISX, Sunnyvale, Calif., USA) having a computer controlled module and interactive menu. This laser uses a mixture of argon-fluoride gas to produce a 193 nm wavelength output of 10 Hz and was adjusted to deliver a fluence at the test surface of 100 to 120 mJ/square cm. The parameters were as follows: energy fluence of 120 mj/cm$^2$; pulse repetition rate 10 Hz. A total of 200 pulses were applied. Lucite was used to calibrate the eximer laser system. Depressions of 100 microns depth and 5.6 mm diameter were made in a lucite template.

The collagen solution (100 µl) was then applied to the depressions and smoothed using a glass slide. Saline solution (3.25 M) was flooded onto the collagen immediately forming a clear gel. The lucite and collagen were then exposed to eximer laser energy to ablate the surface. The ablated area was 5.6 mm in diameter, and the depth of ablation remained at 100 microns indicating that the collagen ablated at the same rate as the lucite.

EXAMPLE 6

Ablation of Enucleated Porcine Cornea Using The Collagen Modulator Solution

In this Example, collagen modulators were evaluated in porcine cornea using the Taunton Technologies Model LV 2000 excimer laser and parameters described in Example 5.

Enucleated porcine eyes were obtained from a local packing house. The eyes were placed in cold sterile saline solution and refrigerated prior to use. Before ablation experiments, the epithelium on the corneal surface was removed using a scalpel blade. An eye was placed in a holder and properly aligned under the eximer laser.

After 600 pulses, an ablation spot of 5.6 mm was formed on the corneal surface at a depth of between 50 and 100 microns (FIG., 8a).

Figure 8A:
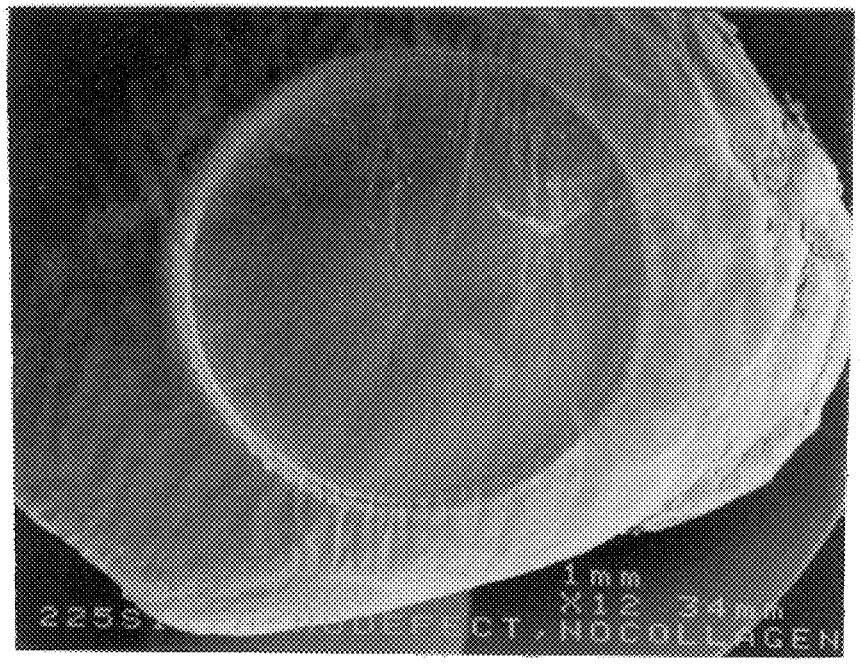
FIG. 8a is an SEM photograph which illustrates the effects of photoablation on a pig corneal surface without the use of a modulator.
Figure 8B:
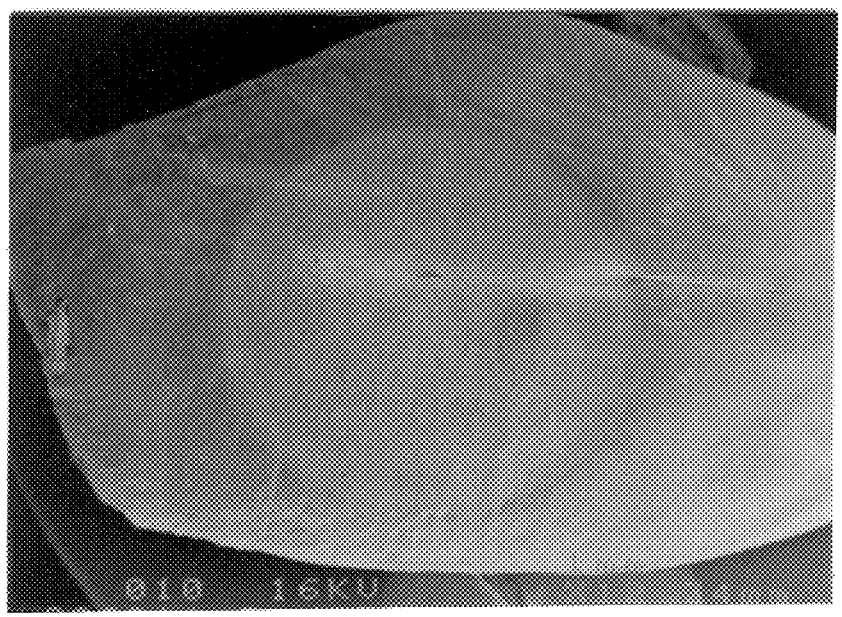
FIG. 8b is an SEM photograph which illustrates the effects of photoablation on a pig corneal surface using a collagen gel modulator.

A 0.1 ml aliquot of a neutralized acid soluble collagen (3.0 mg/ml), prepared in accordance with Example 1, was then applied, using a pasteur pipet, to the deepithelized corneal surface of a second eye. An equivolumne of 3.25 M saline solution was then added, with a pasteur pipet, to the collagen coating. The coating instantly converted into a gel. The photoablation procedure, as described above, was then performed. When a collagen gel modulator was formed on the surface of the porcine cornea, the depth of the ablation spot was reduced by about 75%. The ablation depth was less than 25 microns compared to 100 microns for controls with no collagen (FIG. 8b).

Figure 9A:
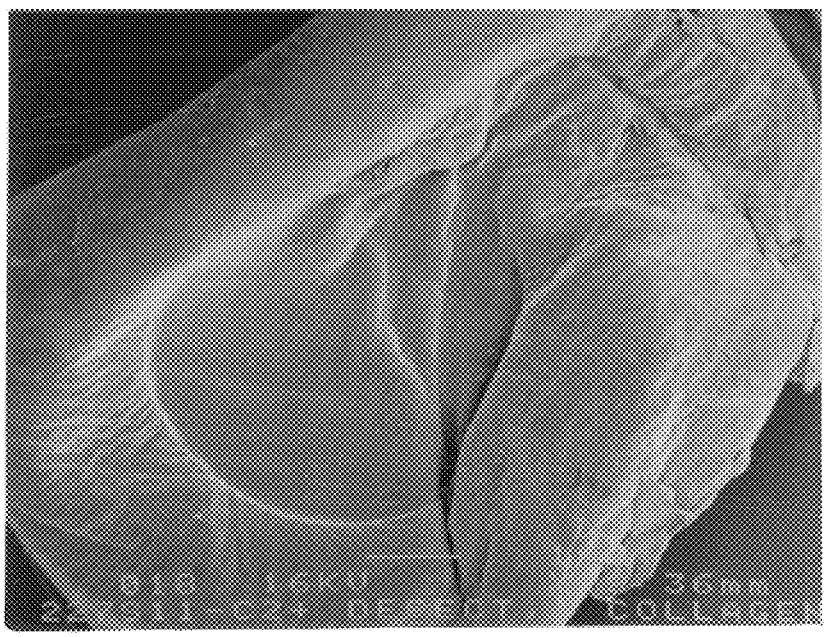
FIG. 9a is an SEM photograph which illustrates the effects of photoablation on a surgically induced irregular pig corneal surface without the use of a modulator.
Figure 9B:
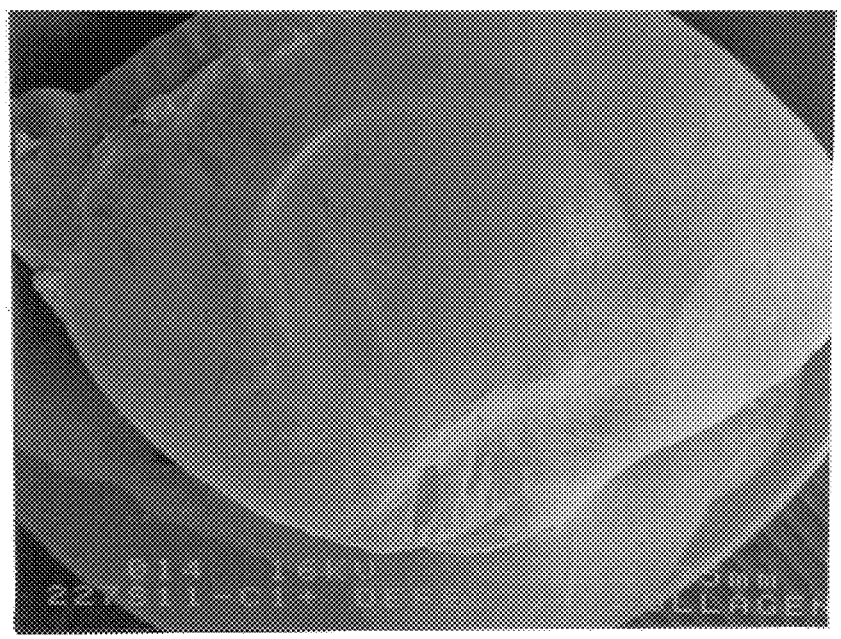
FIG. 9b is an SEM photograph which illustrates the effects of photoablation on a surgically induced irregular pig corneal surface using a collagen gel modulator.

In a separate experiment, crude defects were formed on two porcine corneas using a No. 64 surgical blade. When ablated without a collagen modulator (control eye), using the conditions noted above, the corneal surface became very uneven in the ablation area (FIG. 9a). In contrast, when a collagen modulator was present on the corneal defect, the rough surface became much smoother and more uniform (FIG. 9b) after ablation than the untreated control eye (FIG. 9a). This experiment clearly demonstrated the beneficial effects of using a collagen gel modulator on the corneal surface in providing a smooth uniform surface.

EXAMPLE 7

Figure 10A:
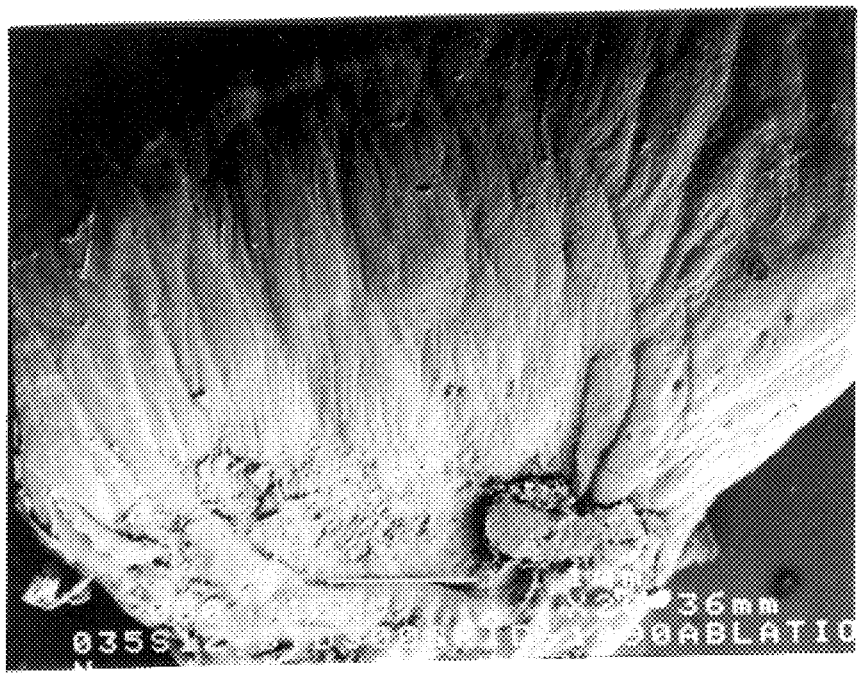
FIG. 10a is an SEM photograph which illustrates the effects of photoablation on a laser induced irregular pig corneal surface using a collagen gel modulator.
Figure 10B:
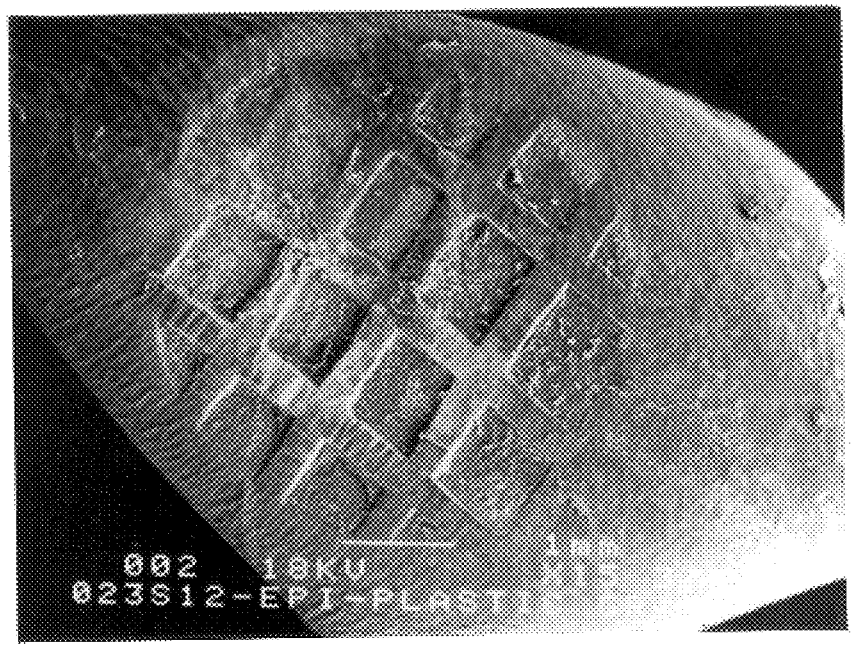
FIG. 10b is an SEM photograph which illustrates the effects of photoablation on a laser induced irregular pig corneal surface without the use of a modulator.

Ablation of an Irregular Porcine Cornea Using a Neutralized Acid Soluble Collagen Modulator Coating In this Example, a 2 cm×2 cm stainless steel or polymer mesh (0.8 mm×0.67 mm) was applied to the surface of a deepithelized pig cornea. Photoablation was initiated and 600 pulses applied using the settings described in Example 5. Ablation results in an impression of the screen in the corneal surface at a depth of about 50 microns. Neutralized acid soluble collagen solution (3.0 mg/ml), prepared in accordance with Example 1, was applied to the surface to fill in the depressions formed by the screen, followed by addition of saline solution as described in Example 6. The eye was then subject to an additional 900 pulses. The collagen modulator appeared to ablate at the same rate as the corneal tissue preventing deepening of the depressions as the screen impression was removed by photoablation (FIG. 10a). When the collagen modulator was absent, the impression of the screen remained after ablation (FIG. 10b). Thus, these experiments clearly demonstrated the beneficial effects of the collagen modulator in providing an important adjunct to photoablation keratectomy.

EXAMPLE 8

Figure 11:
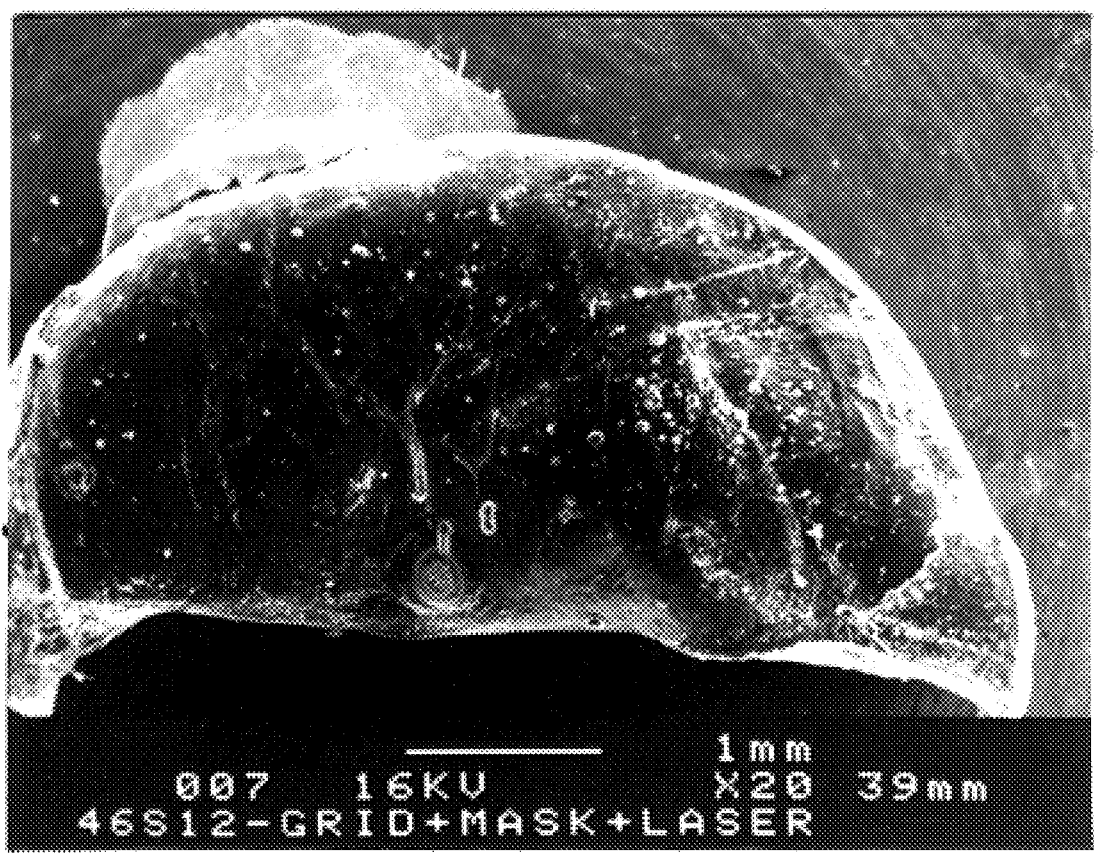
FIG. 11 is an SEM photograph which illustrates the effects of photoablation on a laser induced irregular human donor corneal surface with the use of a collagen gel modulator coating.

Ablation of an Irregular Human Cornea Using a Neutralized Acid Soluble Collagen Modulator Coating In this Example, a human donor eye, rejected for corneal translation, was obtained from the Kentucky Lions Eye Bank. The eye was stored in cold sterile saline buffer at 5° C. Before ablation, the epithelium was removed using a scalpel blade. The eye was placed in a holder and aligned under the eximer laser. A screen impression was made on the deepithelized cornea as described in Example 7. A collagen gel modulator was formed on the cornea and the corneal surface was reexposed to the eximer laser for an additional 900 pulses, as described in Example 5. The results shown in an SEM photograph (FIG. 11) demonstrate the beneficial effects of using a collagen modulator in providing a smooth corneal surface.

EXAMPLE 9

Ablation of an Irregular Porcine Cornea Using a Modified Collagen Modulator Film In this Example, a 2 cm×2 cm stainless steel or polymer mesh (0.8 mm×0.67 mm) is applied to the surface of a deepithelized pig cornea. Photoablation is initiated and 600 pulses are applied using the settings described in Example 5. Ablation results in an impression of the screen in the corneal surface at a depth of about 50 microns. Approximately 100 $\mu$l of a glutaric anhydride modified collagen solution, prepared in accordance with Example 2 and containing 5 wt. % sodium persulfate is applied to the corneal surface with a syringe fitted with a 25 gauge needle to fill in the depressions formed by the screen. Thereafter, the coated corneal surface is subjected to 1.5 minutes of 254 nm UV irradiation at a distance of 4 cm (4 watt portable UV lamp providing 350 microwatts/cm$^2$ intensity at 3 inches, Ultraviolet Products, Inc., San Gabriel, Calif., U.S.A.) to polymerize the glutaric collagen into a thin film. The eye is then subject to an additional 900 pulses as described in Example 3. The collagen modulator appears to ablate at the same rate as the corneal tissue and prevents deepening of the depressions as the screen impression is removed by photoablation. When the collagen modulator is absent, the impression of the screen remains after ablation. Thus, these experiments clearly demonstrate the beneficial effects of the collagen modulator film in providing an important adjunct to photoablation keratectomy.

EXAMPLE 10: Ablation of an Irregular Porcine Cornea Using an Extensively Modified Glutaric Anhydride Collagen Modulator Gel In this Example, a 2 cm×2 stainless steel or polymer mesh is applied to the surface of a deepithelialized pig cornea. Photoablation is initiated and 600 pulses applied using the settings described in Example 5. Ablation results in the formation of an impression of the screen in the corneal surface at a depth of about 50 microns. 100 ul of melted glutaric derivatized collagen solution (37° C.), prepared in accordance with Example 4, is applied to the irregular corneal surface using a syringe fitted with a 25 gauge needle. The collagen modulator forms a firm gel as the collagen equilibrates to room temperature. The eye is then subjected to 900 pulses as described in Example 5. The collagen modulator appears to ablate at the same rate as the intact cornea and prevents deepening of the depressions as the screen impression is removed by photoablation. When the modulator is absent, the impression of the screen remains, and becomes deeper, after ablation. Thus, these experiments clearly demonstrate the beneficial effects of the collagen modulator film in providing an important adjunct to photoablation keratectomy.

EXAMPLE 1: Ablation of an Irregular Porcine Cornea Using a Quinoline Collagen Modulator Film In this Example, a 2 cm×2 stainless steel or polymer mesh is applied to the surface of a deepithelialized pig cornea. Photoablation is initiated and 600 pulses applied using the settings described in Example 5. Ablation results in the formation of an impression of the screen in the corneal surface at a depth of about 50 microns. Approximately 100 ul of a quinoline sulfonyl chloride modified collagen solution, prepared in accordance with Example 4 and containing 5 wt. % sodium persulfate is applied to the corneal surface with a syringe fitted with a 25 gauge needle to fill in the depressions formed by the screen. Thereafter, the coated corneal surface is subjected to 1.5 minutes of 254 nm UV irradiation at a distance of 4 cm (4 watt portable UV lamp providing 350 microwatts/cm$^2$ intensity at 3 inches, Ultraviolet Products, Inc., San Gabriel, Calif., U.S.A.) to polymerize the glutaric collagen into a thin film. The eye is then subject to an additional 900 pulses as described in Example 5. The collagen modulator appears to ablate at the same rate as the corneal tissue and prevents deepening of the depressions as the screen impression is removed by photoablation. When the collagen modulator is absent, the impression of the screen remains after ablation. Thus, these experiments clearly demonstrate the beneficial effects of the collagen modulator film in providing an important adjunct to photoablation keratectomy.

What is claimed is:

1. A method for preparing a collagen modulator on a corneal surface, said corneal surface having depressions, which comprises: applying a neutralized acid soluble collagen solution onto said corneal surface in an amount sufficient to at least fill in said depressions; said neutralized acid soluble collagen solution on said corneal surface having been contacted with an effective amount of at least one metal cation, said metal cation contained in a physiological acceptable solution, so as to convert said soluble solution to a collagen modulator gel.

2. The method according to claim 1, wherein said collagen solution comprises a Type I collagen solution.

3. The method according to claim 1, wherein said metal cation is selected from the group consisting of sodium, potassium, magnesium, and calcium.

4. The method according to claim 1, wherein said metal cation is present in said physiologically acceptable solution in a concentration ranging between about 0.01 M and about 0.05 M.

5. The method according to claim 1, wherein said collagen solution contains between about 1 mg and about 10 mg collagen protein per ml of solution.

6. The method according to claim 1, wherein said corneal surface has been deepithelialized.

* * * * *